United States Patent (10) Patent No.: US 11,130,064 B2
Kahn, II et al. (45) Date of Patent: Sep. 28, 2021

(54) SYSTEMS AND METHODS FOR BIOFEEDBACK GAMEPLAY

(71) Applicant: Neuromotion, Inc., Boston, MA (US)

(72) Inventors: Jason Michal Kahn, II, Arlington, MA (US); Nicholas S. Snietka, Boston, MA (US); Trevor B. Stricker, Boston, MA (US)

(73) Assignee: Neuromotion, Inc., Boston, MA (US)

( * ) Notice: Subject to any disclaimer, the term of this patent is extended or adjusted under 35 U.S.C. 154(b) by 0 days.

(21) Appl. No.: 15/651,814

(22) Filed: Jul. 17, 2017

(65) Prior Publication Data

US 2019/0015751 A1 Jan. 17, 2019

(51) Int. Cl.
*A63F 9/24* (2006.01)
*A63F 13/67* (2014.01)
(Continued)

(52) U.S. Cl.
CPC ............ *A63F 13/67* (2014.09); *A61B 5/0816* (2013.01); *A61B 5/165* (2013.01); *A61B 5/168* (2013.01); *A61B 5/486* (2013.01); *A63F 13/212* (2014.09); *A63F 13/85* (2014.09); *A61B 5/02438* (2013.01); *A61B 2503/12* (2013.01); *A63F 2300/1012* (2013.01)

(58) Field of Classification Search
CPC ........ A63F 13/67; A63F 13/85; A63F 13/212; A63F 2300/1012; A61B 5/486; A61B 5/02438; A61B 5/0816; A61B 2503/12

See application file for complete search history.

(56) References Cited

U.S. PATENT DOCUMENTS 4,149,716 A 4/1979 Scudder et al.
5,001,632 A 3/1991 Hall-Tipping et al.
(Continued)

FOREIGN PATENT DOCUMENTS

WO WO-2001004864 1/2001
WO WO-2013052644 4/2013

OTHER PUBLICATIONS

"Affordable Neurofeedback for your Home, School, & Office", SmartBrain Technology, http://www.smartbraintech.com/, 2017, 2 pages.

*Primary Examiner* — Dmitry Suhol
*Assistant Examiner* — Carl V Larsen
(74) *Attorney, Agent, or Firm* — Strategie Patents, P.C.

(57) ABSTRACT

Techniques are disclosed for deploying game-based therapy correlated with, but independent from, an executing game program. In general, game content within a display can be improved with an overlay of visual therapeutic content such as a visual indicator of a current emotional or physiological state, along with visual features or effects that alter game difficulty. A variety of visual effects can usefully be integrated with third-party game content with requiring direct computation access to the executing game code. For example, effects such as dimming, fading, pixelating, or fogging can be rendered within active regions of a game window independently from, but correlated with the visual content of, the current game. This is suitable for delivering treatment for a range of cognitive and similar disorders and permits rendering of user-specific therapeutic content in combination with third-party games and gaming platforms.

21 Claims, 5 Drawing Sheets

(51) Int. Cl.
A63F 13/212 (2014.01)
A63F 13/85 (2014.01)
A61B 5/08 (2006.01)
A61B 5/00 (2006.01)
A61B 5/16 (2006.01)
A61B 5/024 (2006.01)

(56) References Cited

U.S. PATENT DOCUMENTS

| | | |
|---|---|---|
| 5,246,411 A | 9/1993 | Rackman et al. |
| RE34,728 E | 9/1994 | Hall-Tipping et al. |
| 5,377,100 A * | 12/1994 | Pope ............... A61B 5/0476 341/20 |
| 5,571,057 A | 11/1996 | Ayers et al. |
| 5,839,990 A | 11/1998 | Virkkala et al. |
| 5,860,860 A | 1/1999 | Clayman et al. |
| 5,896,164 A | 4/1999 | Orbach et al. |
| 6,001,065 A | 12/1999 | Devito |
| 6,179,746 B1 | 1/2001 | Delman et al. |
| 6,244,988 B1 | 6/2001 | Delman et al. |
| 6,450,820 B1 * | 9/2002 | Palsson ............ G09B 19/22 434/236 |
| 6,798,461 B2 | 9/2004 | Shapira et al. |
| 8,062,129 B2 * | 11/2011 | Pope ............... A63F 13/06 463/31 |
| 8,308,562 B2 | 11/2012 | Patton |
| 8,814,671 B2 | 8/2014 | Bhogal et al. |
| 8,939,831 B2 | 1/2015 | Dugan et al. |
| 9,084,933 B1 * | 7/2015 | Pope ............... A63F 13/04 |
| 9,498,705 B2 | 11/2016 | May et al. |
| 9,511,289 B2 | 12/2016 | Bond et al. |
| 2007/0066403 A1 | 3/2007 | Conkwright et al. |
| 2007/0149282 A1 | 6/2007 | Lu et al. |
| 2008/0281221 A1 | 11/2008 | Greco et al. |
| 2009/0069707 A1 | 3/2009 | Sandford |
| 2009/0318826 A1 * | 12/2009 | Green ............ A61B 5/04014 600/545 |
| 2010/0125028 A1 | 5/2010 | Heppert et al. |
| 2011/0009193 A1 * | 1/2011 | Bond ............... A63F 13/212 463/36 |
| 2012/0077160 A1 * | 3/2012 | DeGutis ............ G09B 7/02 434/236 |
| 2013/0288777 A1 * | 10/2013 | Short ............... A61B 5/16 463/23 |
| 2014/0004948 A1 | 1/2014 | Watkins, Jr. et al. |
| 2014/0057720 A1 | 2/2014 | Chowdhary et al. |
| 2014/0121017 A1 * | 5/2014 | Mandryk ............ A63F 13/53 463/36 |
| 2014/0206422 A1 * | 7/2014 | Abe ............... A63F 13/814 463/7 |
| 2014/0323013 A1 * | 10/2014 | Gonzalez-Heydrich ............ A63H 29/22 446/484 |
| 2014/0336473 A1 | 11/2014 | Greco |
| 2015/0190709 A1 * | 7/2015 | Moorthy ............ A63F 9/183 463/9 |
| 2015/0282752 A1 * | 10/2015 | Roots ............... A63F 3/04 434/236 |
| 2016/0228029 A1 | 8/2016 | Ware et al. |
| 2017/0025035 A1 * | 1/2017 | Nguyen ............ A63F 13/67 |
| 2017/0045942 A1 * | 2/2017 | Bostick ............ G06F 3/015 |
| 2018/0070872 A1 * | 3/2018 | Simon ............ A61B 5/16 |

\* cited by examiner

SYSTEMS AND METHODS FOR BIOFEEDBACK GAMEPLAY

FIELD

The present invention relates to biofeedback gameplay, and more particularly to systems, methods and computer-program products for modifying gameplay according to physiological feedback from a gamer.

BACKGROUND

Mental health disorders, such as emotional dysregulation, Attention Deficit Hyperactivity Disorder (ADHD), learning disabilities, and other cognitive disorders, have been the subject of numerous forms of treatment, ranging from psychiatric counseling to medicinal treatments. Therapies have also been developed that use computer-based games. While these game-based therapies can provide an engaging medium for therapeutic gameplay, there remains a need for a treatment platform that facilitates the deployment of game-based therapies using third-party game content.

SUMMARY

Techniques are disclosed for deploying game-based therapy correlated with, but independent from, an executing game program. In general, game content within a display can be improved with an overlay of visual therapeutic content such as a visual indicator of a current emotional or physiological state, along with visual features or effects that alter game difficulty. A variety of visual effects can usefully be integrated with third-party game content without requiring direct computation access to the executing game code. For example, effects such as dimming, fading, pixelating, or fogging can be rendered within active regions of a game window independently from, but correlated with, the visual content of the current game. This is suitable for delivering treatment for a range of cognitive and similar disorders and permits rendering of user-specific therapeutic content in combination with third-party games and gaming platforms.

In one aspect, a method is disclosed in which an assessment of a person is received. The assessment may include an evaluation of a trait of the person and an evaluation of an emotional or behavioral impairment of the person. Following the reception of an assessment, a game that is suitable for the person, based on the assessment, may be selected from one or more computer games. The game according to one embodiment may have a variable difficulty. After selection and initialization of the game, a physiological response of the person may be monitored while playing the game and the difficulty of the game may be varied using a pattern based on the emotional or behavioral impairment. A change in the physiological response may be measured as the difficulty of the game changes, and the difficulty of the game may be modified to increase the difficulty when the physiological response exceeds a predetermined threshold characteristic of the emotional or behavioral impairment.

The trait of the person may include a fine motor control, a gross motor control or a cognitive performance skill. The cognitive performance skill may include a working memory, an inhibitory control, or a cognitive flexibility.

The method may include selecting a plurality of computer games and presenting the plurality of computer games to the user as options for gameplay. The assessment may include at least one of a series of questions about the person, a structured evaluation of the person, and a clinical evaluation of the person. Selecting the game may include selecting a computer game suitable for the trait of the person or selecting a computer game to remediate an emotional or behavioral impairment of the person identified in the assessment. The method may also or instead include selecting a computer game suitable for a motor skill of the person. The physiological response may include a heart rate or a breathing rate.

Additionally, the pattern for varying the difficulty of the game may be selected to teach the person improved management of the emotional or behavioral impairment. The pattern for varying the difficulty of the game may also include at least one of: pulsed increases in the difficulty, a piecewise continuous increase in the difficulty, and a ramped increase in the difficulty. Modifying the difficulty may also include changing the pattern, increasing a difficulty of in-game play, or displaying an overlay that obscures a portion of the game presented on a display of a computer. In such a scenario, the system or method may concurrently display an indicator of a degree of manifestation of the emotional or behavioral impairment. Further, according to certain embodiments, modifying the difficulty includes superimposing a graphical element over at least a portion of the game presented on a display of a computer. The graphical element or overlay may include a smoke effect, which may further rise from a bottom of the display to cover an increasing portion of the display as the physiological response indicates increasing manifestation of the emotional or behavioral impairment.

A further embodiment of the invention includes a computer program product for remediating emotional or behavioral impairments. The computer program product includes computer executable code embodied in a non-transitory computer-readable medium that, when executing on one or more computing devices, performs several steps to accomplish the therapeutic goals. Those steps may include receiving an assessment of a person, which includes an evaluation of a trait of the person and an evaluation of an emotional or behavioral impairment of the person. Then a game having variable difficulty is selected from one or more computer games that is suitable for the person based on the assessment. During gameplay, a physiological response of the person is monitored and the difficulty of the game is varied using a pattern based on the person's emotional or behavioral impairment. A change in the physiological response is measured as the difficulty of the game changes and the game is modified to increase the difficulty when the physiological response exceeds a predetermined threshold characteristic of the emotional or behavioral impairment.

Yet another embodiment of the invention includes a system for remediating emotional or behavioral impairments. The system, according to one embodiment, includes a display, a processor, a physiological monitor and a memory. The physiological monitor is configured to provide a physiological signal, the physiological monitor coupled in a communicating relationship with the processor. The memory stores an assessment of a person which includes an evaluation of a trait of the person and an evaluation of an emotional or behavioral impairment of the person. The memory is configured by computer executable code to perform the steps of selecting from one or more computer games having variable difficulty a game suitable for the person based on the assessment. The computer executable code presents the game on the display, monitors a physiological response of the person while playing the game based on the physiological signal from the physiological monitor. The computer executable code varies a difficulty of the game using a pattern based on the emotional or behavioral impairment, and measures a change in the physiological response as the difficulty of the game changes. The computer executable code modifies the difficulty of the game to increase the difficulty when the physiological response exceeds a predetermined threshold characteristic of the emotional or behavioral impairment.

BRIEF DESCRIPTION OF THE DRAWINGS

The above and other objects of the present invention will become more readily apparent from the following detailed description taken in connection with the accompanying drawings, which are provided by way of examples and not limitations.

DETAILED DESCRIPTION

All documents mentioned herein are hereby incorporated by reference in their entirety. References to items in the singular should be understood to include items in the plural, and vice versa, unless explicitly stated to the contrary or otherwise clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

In the following description, it is understood that terms such as "first," "second," "top," "bottom," "up," "down," and the like, are words of convenience and are not to be construed as limiting terms.

The use of the singular herein includes the plural (and vice versa) unless specifically stated otherwise. Moreover, the singular forms "a," "an," and "the" include plural forms unless the context clearly dictates otherwise.

Recitation of ranges of values herein are not intended to be limiting, referring instead individually to any and all values falling within the range, unless otherwise indicated, and each separate value within such a range is incorporated into the specification as if it were individually recited. The words "about," "approximately" or the like, when accompanying a numerical value, are to be construed as including any deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose or the like. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the scope of the disclosed embodiments and does not pose an express limitation on the scope of the following claims. No language in the specification should be construed as indicating any unclaimed element as essential to the practice of the disclosed embodiments.

Figure 1:
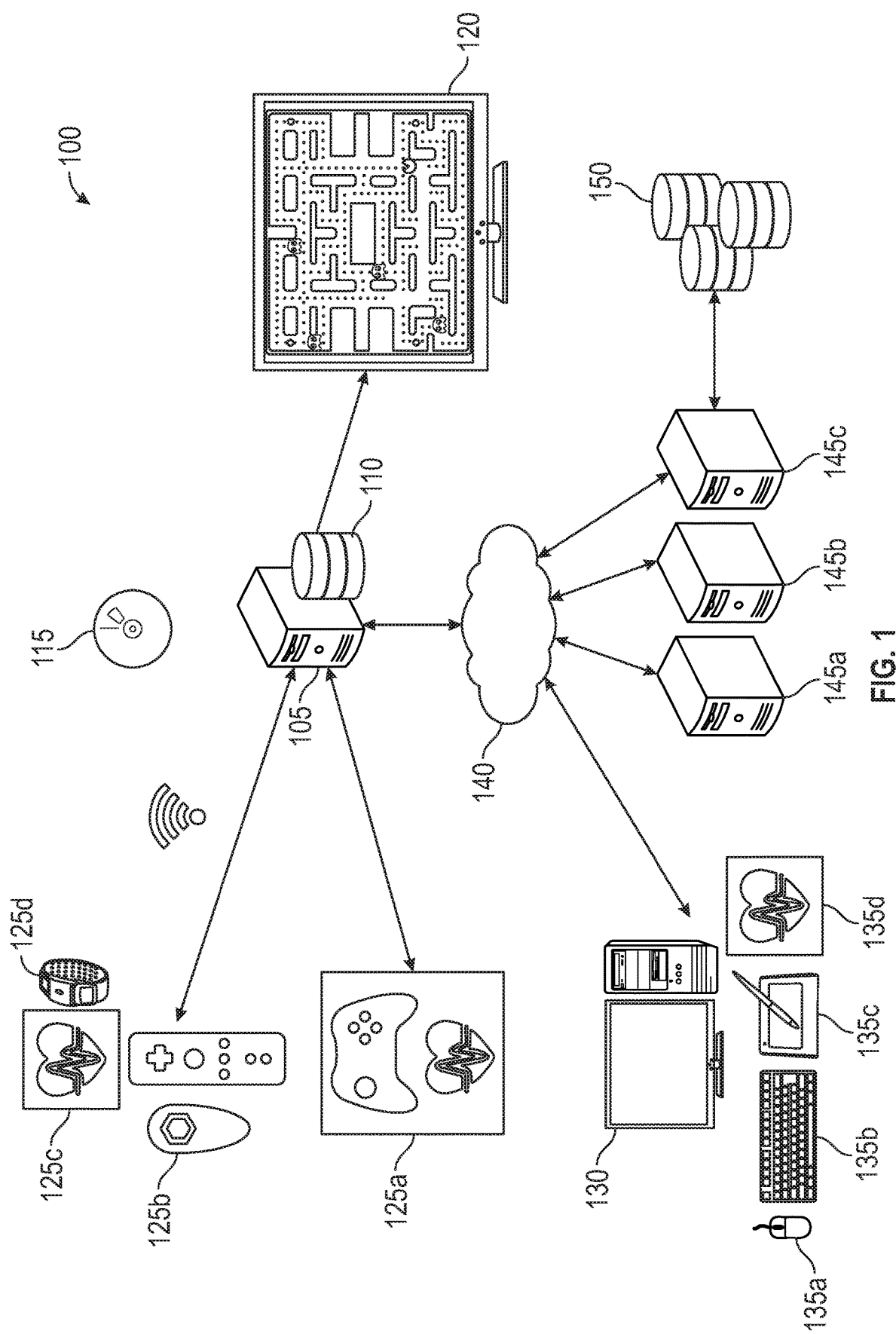
FIG. 1 depicts a system including a number of illustrative game systems and elements.

FIG. 1 depicts a system 100 including a number of illustrative game systems and elements. A game system 105 may include a dedicated gaming console or hardware housing internal memory storage 110 for storing software and data associated with the game system 105 and games played thereon. Additional components of the system may include removable media 115, a display 120, and peripheral devices 125a-d. Alternatively, a game system 130 may be embodied in a multi-purpose computing device such as a personal computer, laptop, tablet or the like, along with peripherals 135a-d. The game systems 105, 130 may connect over a network 140 to one or more servers 145a-c, which may, in turn, be connected to a storage device 150 that stores game content, provides back-end processing, or otherwise facilitates use and operation of the system 100. A game system as contemplated herein may also or instead include a customized system for delivery of therapeutic gaming content in accordance with the details of the embodiments described herein.

Game data and software may be provided in the form of a CD/DVD, Blu-ray disk or other removable media 115 that may be interchangeably inserted and read by the game system 105. Alternatively, game data and software may be stored in the internal memory storage 110. The removable media 115 may also or instead include media stored on USB sticks, flash cards, external hard drives, and so forth (along with suitable connectors, ports, etc.). Additional software for an additional gameplay layer, such as any of those described below, may also be stored on the internal media storage 110 or on the removable media 115, or some combination thereof. The additional software may, for example, include an application or combination of applications that provide a mechanism for recognizing, coaching and modifying behavior associated with emotional disorders by directly or indirectly altering a gameplay environment. Internal memory storage 110 may also store behavioral assessments or reports relating the emotional or behavioral traits, diagnoses and treatment information of a subject, and so forth. Behavioral assessments may also be stored on removable media and inserted into the game system for retrieval.

The display 120 may include a television, monitor, projector or other device to display output of the game system 105 for a user. The display 120 may be directly connected via audio/video cables, such as component, composite, HDMI, USB, DisplayPort cables or may be connected wirelessly via a wireless adapter to the game system 105. Other peripheral devices 125 may be operatively connected to the game system 105 via dedicated cables, such as USB, mini-USB, micro USB, USB-C or other similar data transfer cable, or may be wirelessly connected via Bluetooth, Wi-Fi, or other wireless protocol.

The peripheral devices 125 may include a sensor or sensing system or device for measuring a physiological response and providing a signal indicative thereof. For example, the peripheral device 125a may include a wearable heart rate or pulse sensor such as a wrist-worn or ankle-worn strap that operates as a dedicated physiological monitoring device. In another aspect, a heart rate or pulse sensor may be incorporated into another peripheral device such as a joystick or the like, e.g., by providing contact pads for the palms or fingers of a user. The pulse sensor may be positioned for periodic or constant pulse monitoring according to any of a number of pulse monitoring techniques. The subject's pulse or heart-rate may be detected by the sensor and a signal indicative of the corresponding physiological condition may be transmitted by the peripheral device 125 to the game system 105 for analysis and use in modifying a gameplay experience of the subject. Alternatively, the sensor of the peripheral device 125 may take the form of a separate device working in conjunction with another peripheral device 125. For example, a discrete heart-rate or pulse monitor 125c (e.g., using a chest strap or other contacts and leads attached by adhesives) or fitness type bracelet 125d may be used in combination with a game controller 125b, e.g., by providing a physiological signal to the game controller 125b, which may in turn be processed as appropriate and transmitted to the game system 105. The physiological sensor(s) may monitor responses other than pulse or heart-rate. For example, the sensor may be configured to monitor movement, temperature, eye-movement, breathing and so forth, and to transmit signals indicative of the monitored physical response to a game system 105 or other computing device.

More generally, the peripheral devices 125 may include any sensor or combination of sensors suitable for physiological monitoring including, without limitation, optical sensors, imaging devices, inertial sensors, capacitors, resistors, thermistors, and so forth. As generally contemplated herein, the monitored physiological response may be used to detect relevant emotional states or the like, such as agitation or increased stress.

It will be appreciated that the specific physiological response(s) may vary according to the condition being addressed with therapeutic gameplay, as well as the individual tendencies of a particular user, which may usefully be monitored over time for improved customization. For example, biofeedback may usefully be incorporated into therapeutic gameplay addressing Attention Deficit Hyperactivity Disorder, Learning Disabilities, Cognitive Effects of Aging and other cognitive disorders, emotional disorders or conditions, learning disabilities and so forth. Thus, the particular types of monitors used, the physiological states that are monitored, and the elevated, unregulated or out-of-normal conditions that are detected, may vary significantly from application to application. However, one of ordinary skill in the art will readily appreciated the scope of conditions amenable to gameplay therapy, as well as the associated physiological states and normal or out-of-normal ranges for each. Thus, the present description generally avoids discussions of particular conditions and particular thresholds for corresponding physiological states. Nonetheless, the concepts disclosed herein are generally applicable to any condition amenable to gameplay therapy using computer video games in combination with monitoring and feedback of associated physiological states.

The game system 130 may also be deployed on a general purpose computer that is used for other computer functions in addition to video gameplay. Like the game system 105, the game system 130 may include internal storage (not shown) as well as internal memory for receiving and storing data from removable media such as CD/DVD or Blue-ray disks. The system may also include inputs and ports for other types of removable media such as media stored on USB sticks, flash media, or external hard drives. Further, game system 130 also may include a variety of wired or wireless peripherals 135, such as a mouse 135a, a keyboard 135b, a touchpad 135c, or a physiological monitor 135d, to provide input to the computer system 130.

The game systems 105, 130 may be connected to a network 140 such as a wide area network (WAN) or local area network (LAN). The game systems 105, 130 may, periodically or in real-time, transmit data over the network 140 to one or more servers 145a-c. The servers 145 may be remotely located or may be located on the same premises as the game systems 105, 130. The servers 145 may analyze data transmitted from the game system(s) 105, 130 and apply this data to an emotional learning platform or algorithm that uses the sensor data and game performance data to develop, create, modify and improve diagnostic and educational tools for future treatment programs. The servers 145 may be connected to storage devices 150 where sensor data, game performance data, behavioral assessments, and other data are stored for analysis and preservation.

Figure 2:
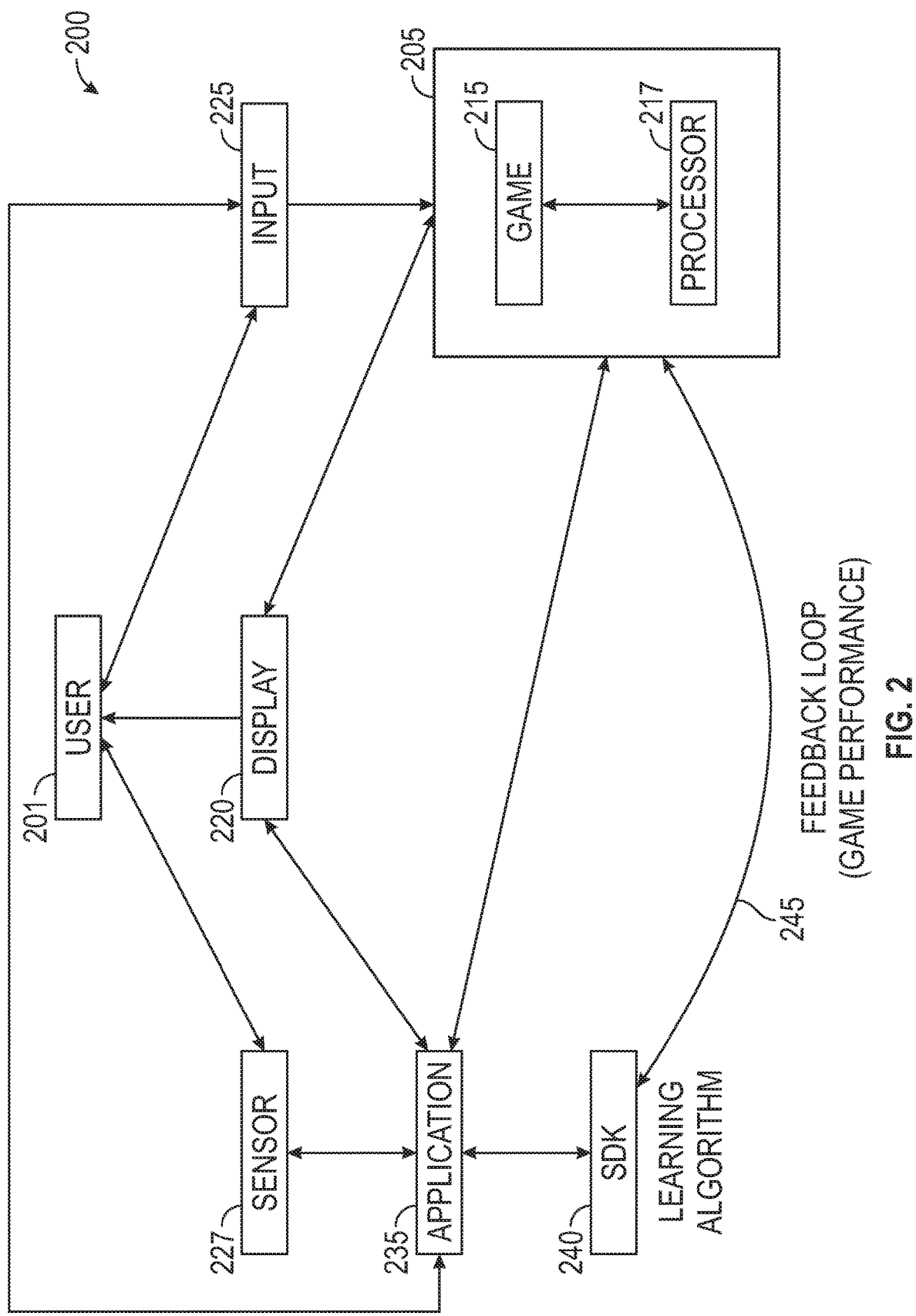
FIG. 2 shows a gameplay environment.

FIG. 2 shows a gameplay environment. The gameplay environment 200 may include, without limitation, a user 201, a game system 205, an input device 225, a sensor 227, a display 220, an application 235, a software development kit ("SDK") 240, and a feedback loop 245.

A user 201, referred to interchangeably herein as user, player, subject, person or patient, interacts with an input device 225 and a sensor 227 during gameplay that is presented to the user on a display 220. The input device 225 and sensor 227 may, for example, include any of the peripheral devices and physiological monitors described above, and may be physically housed in the same device or in separate devices that communicate with one another or with the game system 205.

During gameplay, the user 201 may interact with the input device 225 to control gameplay. The input device 225 may be a joystick, keypad, touchpad, motion controller, motion sensor, microphone or other peripheral device or combination of devices configured to receive user input from the user 201 and transmit corresponding input signals to the game system 205. In general, the game system 205 may include game media 215 and a processor 225 configured to execute the gameplay based on the game media 215 and input signals received from the input device 225. The game media 215 may be stored in a memory associated with the game system 205 such as internal storage, external storage or removable media. The system 205 may output a visual presentation of the gameplay to the display 220.

A software development kit (SDK) 240 may be implemented to provide tools for creation, deployment and execution of an application 235 to interface with various components of the gameplay environment 200. The SDK 240 may generally be used to generate applications 235 that incorporate physiological feedback into third-party game content, such as to monitor, control and teach behavior modification and emotional regulation as contemplated herein. The SDK 240 may usefully support applications 235 that are implemented over the top of the third-party game, e.g., without having to access the encoded software code of the game. By facilitating deployment in this manner, the SDK 240 can facilitate the use of physiological feedback for therapeutic gameplay with commercially available video games.

The application 235 may interface with various components of the gameplay environment 200 to achieve the therapeutic goals contemplated herein. During gameplay, the application 235 may receive input from the sensor 227 and, based on physiological signals or other data obtained from the sensor 227, may affect the gameplay environment 200, e.g., by providing video overlay for game content in the display 220. For example, the application 235 may provide supplemental video or audio content alerting the user 201, or an observer, that the user 201 is experiencing emotional dysregulation or other behavioral reaction that requires attention or correction. A user 201 may become emotionally agitated, angry, frustrated, or otherwise dysregulated when faced with certain challenges presented by the game 215. The system may be designed to alert the user 201 of the change in emotional state so that the user 201, rather than continue in a state of dysregulation, may take remedial action to return to a state of emotional regulation. As detailed above, the emotional dysregulation may be detected through the measurement of any number of physiological responses. For example, if a user 201 becomes agitated during gameplay, the user 201 may exhibit a pulse rate increase, a skin or body temperature increase, sweating (which can be measured, e.g., through a galvanic skin response), changes in breathing rate, a temporary cessation of breathing, twitching or unexpected physical movements, and so forth, any of which may be detected, either alone or in combination, by any of the various types of sensors described herein, and used to evaluate an emotional or physical state of the user 201. Thus, the sensors may include heart rate sensors, skin temperature sensors, muscle tension sensors, brain activity sensors, electroencephalographs, electromyographs, skin conductance sensors, and any other sensor or combination of sensors suitable for generating actionable biofeedback in a therapeutic gameplay context.

The application 235 may generally monitor signals from the sensor 227, and may generate output to responsively control the gaming environment 200.

In one aspect, the application 235 may superimpose or overlay a graphical element on the display 220 indicative of the user's emotional or physiological state. Such an indicator may take the form or a colored shape, symbol, word, numerical value or other indicator. For example, if the user is not experiencing an adverse emotional state, a green balloon, circle or other indicator may be superimposed on a portion of the display screen 220. When the sensor 227 transmits a change in the physiological response being measured, the application 235 may determine if the response exceeds a given threshold indicating the onset of an adverse emotional state. The application 235 may then change the indicator to reflect a change in the user's emotional state. For example, the green balloon may turn to a yellow or red balloon, depending on the severity of the change. In another aspect, the indicator may be presented as a status bar or a gauge with a moving needle that adjusts to a detected physiological or emotional state. For example, the moving needle may continuously adjust to a monitored physiological condition, and the gauge may be color coded or otherwise visually marked to indicate a relative severity of a physiological state. Using this or any other suitable visualization techniques, the application 235 may provide visual feedback to the user 201 about a current physical or emotional state of the user 201.

The user 201, upon seeing the indicator displaying an out-of-normal physiological response as indicated, e.g., by a gauge at a red or near maximum position, may become cognizant of an unregulated emotional state and take remedial action. If remedial action is successful and the sensor 227 reports a physiological response within the allowed parameters, the application 235 may return the indicator back to a more favorable state (e.g., green). In addition to the visual indicator, the application 235 may provide other cues to an undesirable emotional or physical state based on the monitored physiological condition(s). For example, the application 235 may provide audio cues, haptic cues, and so forth. In general, the indicator may present binary, staged, or continuous indicators of emotional regulation/dysregulation, along with suitable audio and/or visual cues.

In addition to providing user feedback on an emotional and physical state as contemplated above, the application 235 may affect gameplay difficulty upon detection of a threshold-exceeding physiological response, e.g., a response indicative of an elevated or unregulated emotional or physical state. For example, the application 235 may deploy any of a number of visual elements within a game window in the display 220 during gameplay to obstruct a view of gameplay and render user responses more difficult. These visual elements may, for example, include: blocking out the display or a portion of the display, dimming the display, blurring the display, pulsing the display, flashing the display, coloring the display, or displaying a pattern overlay on the display. In one aspect, a smoke screen or other visual effect may rise from the bottom or some other edge of the window to slowly obscure portions of the game screen while the emotional or physical state remains unregulated. In another aspect, clouds may move about to partially or wholly obscure relevant portions of the game window. Other visual techniques may also or instead be employed. For example, some or all of the game window may be pixelated to reduce the resolution of graphics rendering. For mild pixelation, this may not affect gameplay substantially, but as effective pixel sizes become larger and larger, the detail necessary for effective gameplay can become obscured or entirely lost. Similarly, a cloud or the like may become increasingly more opaque to render game play progressively more difficult in response to certain biofeedback from the sensor 227. This general technique of visual obfuscation may be used to render gameplay more difficult in response to inappropriately elevated emotional states. These and other visual effects may be implemented individually, or may be combined with other disruption techniques described below, including additional visual disruptions, audio disruptions, or system disruptions. Further, these effects may be executed across the entire display, may be selectively implemented over a portion of the screen, or may be implemented as moving effects rippled or moved across the display.

The application 235 may also utilize audio alterations to affect gameplay. For example, the application 235 may eliminate, dampen, muffle, pulse, distort, replace, or otherwise alter the sound, which may render gameplay more difficult where the game requires responses to audio cues. The application 235 may also or instead provide an audio indicator to the user 201 of an inappropriate or undesirable physiological response, or more generally that an emotional or physiological threshold has been exceeded.

The application 235 may also or instead control gameplay difficulty by affecting the input device 225 in response to a dysregulation event or other behavioral trigger. For example, upon detecting a threshold-exceeding physiological response from the sensor 227, the application 235 may interrupt, disable or otherwise disrupt gameplay by altering the signals from the input device 225 to the game system 205. The changes to the signal may directly or indirectly affect how the input signal is received and processed by the processor 225 making the gameplay more difficult. These interruptions to the game 215 may include, without limitation, rejecting, reversing, increasing the speed, lagging, amplifying, dampening, or introducing an error or jitter into the input signal sent from the input device 225. For example, if a dysregulation event is detected, the application 235 may interrupt the signal from the input device 225 to the game system 205 by adding an additional delay between the time an input device button is actuated and the time it is processed by the game system 205 and its effects are shown on the display 220. A user 201 currently experiencing dysregulation may press a button of the input device 225 in the course of gameplay, and the input may be lagged to further adversely affect gameplay in response to an emotional or physical state of the user 201, thereby making the game more difficult to the user 201. To return the input device 225 (and/or display 220) to its normal and undisrupted state, the user must first remediate his or her behavior such that the sensor 227 detects and reports a return to an acceptable physiological response. These exemplary disruptions to the input control may also be used in conjunction with other disruptions.

Disruptions to gameplay may also be managed through the game system 205 and the processor 217. For example, upon detection of a dysregulation event, or other disfavored behavioral event, the application 235 may affect the ability of the processor 217 to execute the game 215. The application 235 may be configured, for example, to cause the processor 217 and its clock to slow down, speed up, or stop during gameplay. The application 235 may also affect the frame rate output by the processor 217 to reduce or increase the rates at which the video frames are rendered to or presented on the display 220.

A feedback loop 245 may be provided from the game system 205 to the SDK 235 to provide game performance and sensor data to feed an emotional learning algorithm. The emotional learning algorithm may update and personalize existing content and gameplay, or may be used to generate new content or gameplay to be used in future treatment regimens. The data obtained and recorded by the sensors 227, application 235 and the game system 205 may provide useful data to customize, improve and advance the provided treatments for the current user as well as other users who may exhibit or experience similar responses during gameplay. The gameplay and sensor data may be stored in a cloud-base environment, where the data is accessed, retrieved, and used by a large community of treatment providers. The stored data may be anonymized to remove any personal or otherwise identifying information.

Figure 3:
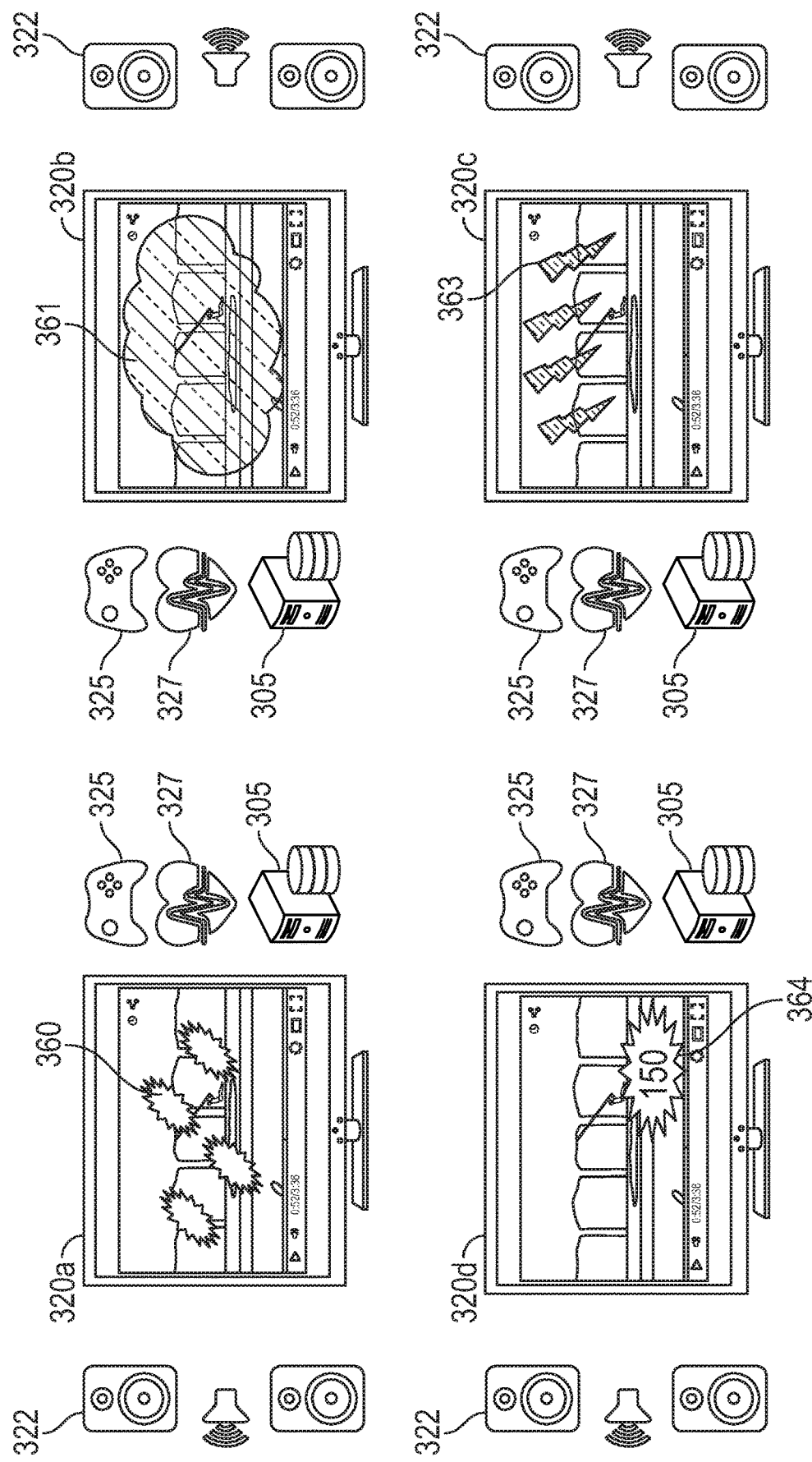
FIG. 3 depicts a series of illustrative displays and gameplay environment components.

FIG. 3 depicts a series of illustrative displays 320*a-d* and gameplay environment components. The gameplay environment may include one or more of: an input device 325 such as a game controller, joystick or the like, a sensor 327 for physiological monitoring of a user, a gameplay system 305 such as a personal computer, tablet, or dedicated gaming console, a display 320, a speaker 322, and any other suitable hardware for use in the gameplay environment. If a threshold-exceeding physiological response is detected by the sensor 327, an application for responsively controlling a difficulty of game content may visually obstruct graphical game content, e.g., by overlaying a series of balloons, explosions, clouds, smoke or other visual effects 360 to partially obscure portions of the gameplay display. When these visual effects 360 are superimposed on the display 320, the gameplay becomes more difficult due to the obstruction of a portion of the screen. These visual effects 360 may be used alone or in combination with one another and/or other disruption techniques described herein.

A gameplay disruption may, for example, be in the form of a smokescreen or cloud 361 superimposed on the gameplay screen 320*b*. The smokescreen 361 may be displayed with a varying level of transparency or color to indicate the severity of the dysregulation event. For example, if the physiological response is only slightly above the set threshold, the smokescreen 361 or other visual effect 360 may have a high degree of transparency, allowing the user to still see most of the game in the display screen 320*b* and to continue gameplay with little negative impact. If the physiological response exceeds the set threshold, the smokescreen 361 may be near opaque making any gameplay nearly impossible. The smokescreen or cloud affect may also be presented gradually as a vertical or horizontal curtain where a portion of the smokescreen 361 is displayed at the bottom or some other edge of the display and the smokescreen 361 gradually moves across the display 360*b* to progressively obscure an increasing portion of the display 360*b* in response to an increasingly elevated emotional or physical state. Alternatively, the application may create flashing or sporadically displayed disruptions that increase the difficulty of the gameplay by intermittently obstructing portions of the gaming window. For example, a series of lightning bolts 363 or other flashing overlays may be displayed on the display 320*c*. These overlays may also be used in conjunction with audio indicators, such as thunderclaps or other audio disruptions emitted from the speakers 322.

Further, the application may present an indicator of physiological state or response. For example, the application may generate a continuously displayed badge or balloon indicator 364 that constantly displays a physiological response of the user on a portion of the display 320*d*, preferably in a location that does not otherwise obstruct gameplay. This indicator provides an explicit indicator of dysregulation events or the like, and can promote self-learning about triggers and aggravating contexts for elevated responses, as well as an explicit signal for initiating remediation strategies.

A variety of animation techniques may usefully be employed to provide an in-game indicator of physiological state. For example, a dial, gauge, or status bar may be provided to indicate normal and elevated regions of physiological response. The indicator may be color coded, e.g., with a green region for normal responses, a yellow region for slightly elevated responses, and a red region for highly elevated or inappropriate responses. In another aspect, a colored balloon may be used to progressively indicate levels of physiological stress or response. In this latter example, the balloon may transform in shape or size when the sensor 327 detects an unacceptable or inappropriate rise in the physiological response. For example, the static balloon may change colors, begin to flash, transform into a smokescreen or otherwise provide a visual alert about an elevated physiological state.

The visual techniques described herein may usefully be deployed independently from gaming software by writing visual effects directly to a display (or a video buffer for a display). While the remedial content is preferably coordinated with the game content, e.g., by obscuring appropriate portions of the screen and creating progressively more difficult game play, it is not necessary to modify original game content in order to use these techniques. Thus, as a significant advantage, the techniques contemplated herein can be deployed over third-party gaming content without modifying the third-party gaming content. In order to coordinate the delivery of visual effects, the application may usefully receive game status information in any of a number of ways. For example, where the third-party game program provides an application programming interface that provides game status or other information, this explicit game output may be monitored to determine game status or progress. In another aspect, the game status may be directly inferred from the visual display of an in-progress game, e.g., by screen scraping, automatic content recognition, or otherwise programmatically monitoring the visual progress of a game. Thus, a variety of techniques may be employed to monitor game progress along with a physiological response of a user, and to responsively control the deployment of visual effects within the game context.

In one aspect, the third-party gaming content may provide an application programming interface that permits control of gaming difficulty. In this case, the application programming interface may be used by the biofeedback application to directly control difficulty of game play for the purposes contemplated herein. Even in this latter embodiment, the system may usefully integrate a visual indicator such as a dial, gauge or the like that provides explicit visual feedback to a user of elevated and/or inappropriate physiological responses. Thus, the systems and methods contemplated herein may usefully integrate in a number of ways with third-party gaming content in a manner that does not require modifications to the third-party software.

Figure 4:
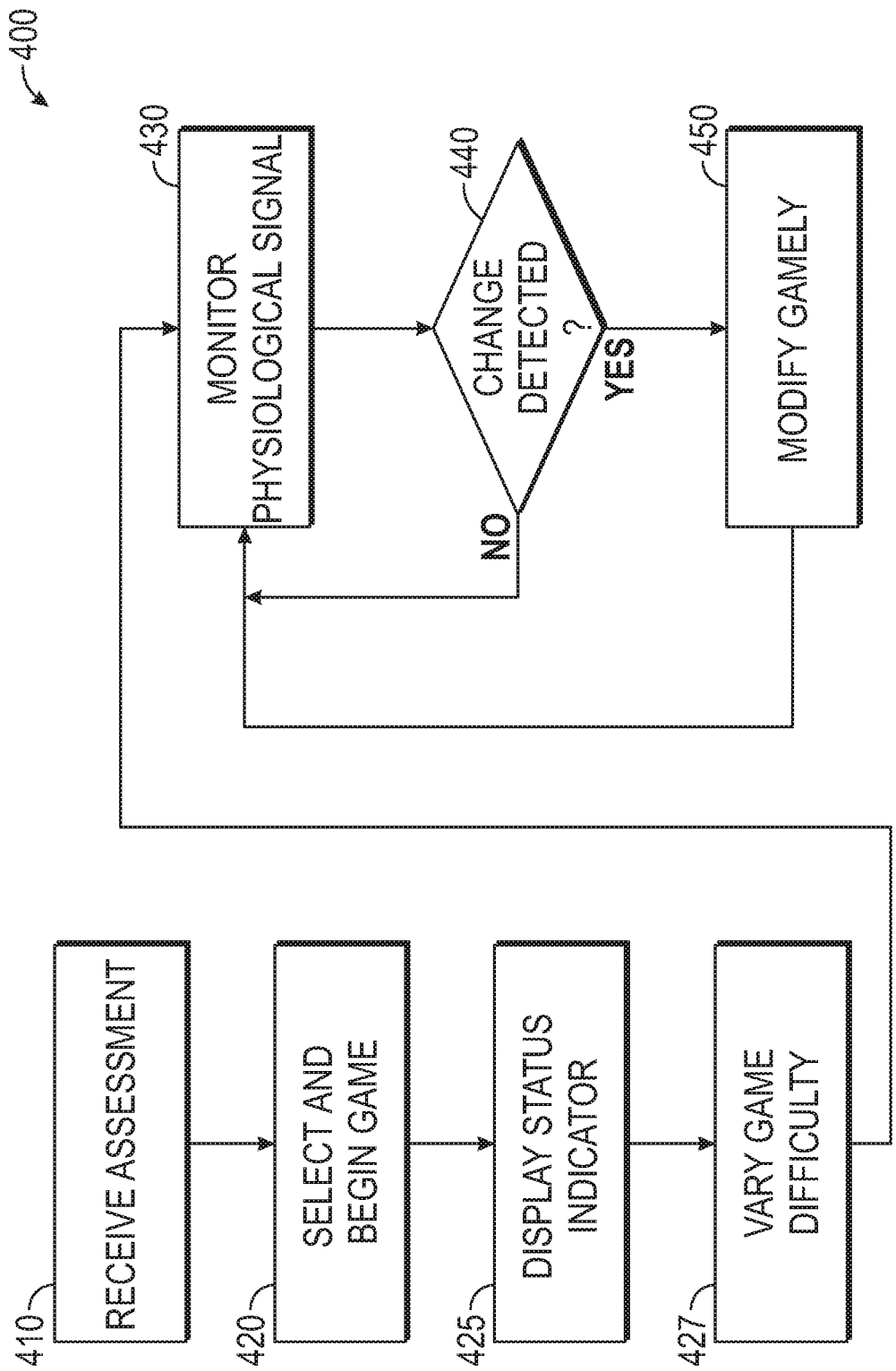
FIG. 4 shows a flow chart of a method of providing biofeedback gameplay.

FIG. 4 shows a flow chart of a method of providing biofeedback gameplay. As shown in step 410, the method 400 may begin with receiving an assessment of a person or user. The assessment may, for example, include an evaluation of a trait of the person and an evaluation of an emotional or behavioral impairment of the person. The assessment may be stored in a database or other record management system to which the application or SDK may access upon initialization of the system. According to one embodiment, initialization to the system will present the user with a login or registration screen, which upon entering the required information, such as a login, PIN, password or other personal identifier may retrieve an assessment of the user.

The trait may be any trait relevant to the assessment of an impairment or the management of therapeutic gameplay. For example, the trait may include motor control, such as fine motor control or gross motor control. The trait may also or instead include a cognitive performance skill such as perception, attention, working memory, language, visual and spatial reasoning, executive function or inhibitory control, cognitive flexibility and so forth. These traits may be useful in determining an appropriate therapeutic strategy for controlling gameplay. However, other traits may be relevant to game selection independently from (or in combination with) selection of therapeutic strategy. For example, conditions such as dyslexia or impaired motor control may render particular games or game types more stressful or challenging due to the nature of the physical condition. In this case, other games might be selected to provide a more useful platform for deploying therapeutic game content.

The emotional or behavioral impairment of the person may be assessed in a number of ways including automated assessment, self-assessment, or clinical assessment. In one aspect, the assessment may include a series of questions about the person, which may be administered by a healthcare professional or self-administered via an online or computerized test. In another aspect, the assessment may include a structured evaluation or a clinical evaluation of the person, e.g., by a suitable trained professional. In this context, receiving an assessment may include receiving an assessment by personnel who can configure the gaming environment appropriately, or programmatically receiving the assessment in any form by an SDK or biofeedback application in a manner suitable for controlling therapeutic gameplay.

A user's assessment, for example, may detail the onset of emotional dysregulation coinciding with an increase in pulse rate above a given threshold. The application or SDK may receive the assessment and determine an appropriate pulse rate threshold for identifying an unregulated condition. Gameplay may begin and the sensors will continuously monitor the user's pulse rate. If the sensor detects and reports a heart rate above the pre-set threshold, the application may execute any number of disruptions to make the gameplay more difficult to the user as generally described above.

As shown in step 420, the method 400 may include selecting a game having a variable difficulty. The game may be selected from one or more computer games to be suitable for the person based on the assessment. The game may, for example be one of several games stored in a database within the game system itself, stored on removable media such as a CD/DVD or Blu-ray disk, or obtained over a network through connections to a server. Games and game data may be stored in combinations of local storage, removable media or over the network. Selecting the game may include selecting a computer game suitable for remediating an emotional or behavioral impairment of the person identified in the assessment.

The game may generally provide varying degrees of difficulty, independent from adjustments to difficulty provided by the biofeedback application described above. That is, the game may include increasing levels of difficulty in gameplay to provide increasing challenges to the user.

As noted above, the type of game may be selected as suitable based on traits of the user. For example, where a user has specific impairments such as dyslexia or impaired memory, games may be selected that are not inherently more challenging for that condition. This approach may usefully permit the selection of appropriate games, specifically so that a user is not so inherently challenged by the game construct that it becomes difficult or impossible to independently manage a variable, biofeedback-based game difficulty. For example, a game may be selected to be suitable for a motor skill of the person, a memory/recall ability of the person and so forth.

In another aspect, selecting a computer game may include selecting a plurality of games, such as games suitable for a particular emotional or behavioral impairment, and then presenting the plurality of games to the person as options for gameplay. The person may then select one of the plurality of games for current use, e.g., in a user interface of a game system. Once a suitable game is chosen and loaded the gameplay experience may begin.

As shown in step 425, the method 400 may include concurrently displaying an indicator of a degree of manifestation of the emotional or behavioral impairment during gameplay. This may include any of the indicators described above.

As shown in step 427, the method 400 may include varying a difficulty of the game according to an intended therapeutic effect. This may for example, include varying the difficulty using a pattern based on the emotional or behavioral impairment identified in the assessment for the person playing the game. In one aspect, this may include directly controlling difficulty of the third-party game content, or permitting inherent increases in game difficulty for the third-party game content to provide a stimulus for triggering unregulated responses or the like. In another aspect, this may include deploying any of the disruptions or similar techniques described above to increase game difficulty in a manner designed to trigger a response related to the impairment.

In one aspect, the pattern for varying the difficulty of the game is selected to teach the person improved management of the emotional or behavioral impairment. In another aspect, the pattern for varying the difficulty of the game includes at least one of pulsed increases in the difficulty, a piecewise continuous increase in the difficulty, and a ramped increase in the difficulty. It will be understood that these patterns, while described here in the context of an initial variation in game difficulty, may also or instead be applied to modify gameplay as described in step 450 below, where difficulty may be further modified using any of these techniques to teach improved management of an emotional or behavioral impairment on an ongoing basis during gameplay.

As shown in step 430, the method 400 may include measuring a physiological response of the person as the difficulty of the game changes. For example, the physiological response may include a heart rate, a breathing rate, or any other physiological response potentially indicative of an elevated emotional or physiological state. This may, for example, include monitoring a physiological signal from any of the sensors described above. During gameplay, a physiological response of the user may be monitored using, e.g., a sensor integrated into the hardware of the controller or otherwise positioned to monitor a physiological response of the user. For example, a pulse sensor may be optimally placed in the housing of the controller to reside in a location common to the placement of a user's thumb. Temperature sensors, gyroscopes, accelerometers and other physiological measurement devices may be used instead of, or in conjunction with, a pulse sensor to obtain different or additional physiological responses during gameplay. A gameplay system may be implemented using motion capture or camera detection capabilities. For example, a camera may be used to track or monitor the movements of the controller, and thus the movements of the player. The controller may include a receiver device capable of being detected and tracked by the camera connected to the system.

Alternatively, the physiological sensor may be separate from the game controller. In such a configuration, the stand-alone sensor device may be in communication with the remediation application and gameplay system though either a wired or wireless connection. Examples of stand-alone sensor devices may include, but are not limited to, wearable devices such as wristbands, headbands, rings, patches, or any other devices attachable or affixable to a user and configured to monitor a physiological response.

As shown in step 440, it may be determined if a change is detected in the physiological response. If no change is detected, or if the changes are within normal ranges, then the method 400 may return to step 430 for continued monitoring, and gameplay may continue in an unmodified form. If a change is detected, such as a change beyond some threshold or window for normal, expected variations, then the method 400 may proceed to step 450 and gameplay may be modified in response. As noted above, the specific signal values will vary according to the type of impairment and the individual person being monitored. Thus, in the present context, specific values are not provided, but it will be readily appreciated to one of ordinary skill in the art what type of physiological signals might be monitored, and what signal levels will be indicative of normal or out-of-normal for a particular person and type or severity of impairment.

As shown in step 450, the method 400 may include modifying the difficulty of the game to increase the difficulty when the physiological response exceeds a predetermined threshold characteristic of the emotional or behavioral impairment. The predetermined threshold characteristic may be a threshold specific to the person playing the game, specific to a condition or impairment of the person playing the game, or some combination of these.

Numerous therapeutic strategies may be employed to modify game play as contemplated herein, any of which may be used to further vary game difficulty in an ongoing manner according to physiological feedback from a person playing the game. For example, gameplay be modified using any of the patterns or strategies described above with reference to step 427. Modifying difficulty may also or instead include changing the pattern for varying difficulty over time, e.g., in response to improving or worsening user performance.

Modifying the difficulty may also or instead include modifying the difficulty in response to the detected physiological state using any of the techniques described above. This may include increasing a difficulty of in-game play, either using difficulty controls for the gaming software available through an application programming interface or by deploying the visual modification techniques described above. For example, modifying the difficulty may include displaying an overlay that obscures a portion of the game presented on a display of a computer. The overlay may include a smoke effect or the like, which may rise from a bottom of the display to cover an increasing portion of the display as the physiological response indicates increasing manifestation of the emotional or behavioral impairment. The method may also or instead include superimposing a graphical element over at least a portion of the game presented on a display of a computer such as any of the graphical or visual elements described above. In another aspect, modifying the difficulty may include altering the sound effects or audio during gameplay by, for example, changing volumes, adding additional audio indicators, muffling or amplifying sound effects or the like. In yet another aspect, modifying the difficulty may include modifying the responsiveness of input devices such as buttons, joysticks, touchpads, keyboards or the like to impose delay, jitter, or the like on physical input actions by a person playing the game with the input device(s).

Modifications may be incremental or continuous. In this context, an incremental modification refers to a single, one-time, and one-directional modification of screen content, such as by sliding a cloud an incremental step over an additional portion of a display. The next incremental modification may cover more or less of the screen according to an instantaneous measurement of the monitored physiological signal. By contrast, a continuous modification as contemplated herein includes a deterministic modification that proceeds for a predetermined duration toward a defined result, e.g., where in response to an elevated physiological state the cloud proceeds to cover one third of the game display with a twenty-five percent opacity in a slow-moving animation. Once the defined result is reached, the user's physiological state may once again be measured, and the modification may advance, retreat or remain according to the new measurement.

After a modification to difficulty has been made, the method 400 may return to step 430 where monitoring may continue until additional changes are detected. The method 400 may continue in this fashion for the duration of a gameplay session, which may include any number of games.

Any of the previously described disruption methods, alone or in combination, may be implemented upon detection of an unacceptable physiological response. The gameplay disruptions may continue to make gameplay more difficult until the continuously monitored physiological response has returned to an acceptable level. For example, if the physiological trigger is tied to a user's pulse rate, the application may continue to disrupt gameplay until the sensors have detected and reported a physiological response that has returned to an acceptable level. At such time, the application may cease the disruptions and return gameplay to its normal state. The sensors and application will continue to monitor the physiological response as gameplay continues.

The nature and duration of the disruption may also be controlled in other ways. For example, after a prolonged interval of elevated physiological response, it may be determined that no favorable resolution of the undesirable response will be achieved, and the game may terminate, or return to normal gameplay. In this case, the user may be directed to supplemental materials or exercises to advance therapy or otherwise address the matter. In another aspect, the duration and severity of disruptions may be customized for a particular person based on a history of responses and remediation. More generally, the systems and methods described above may be adapted with any strategies or techniques consistent with the therapeutic objectives contemplated herein.

Figure 5:
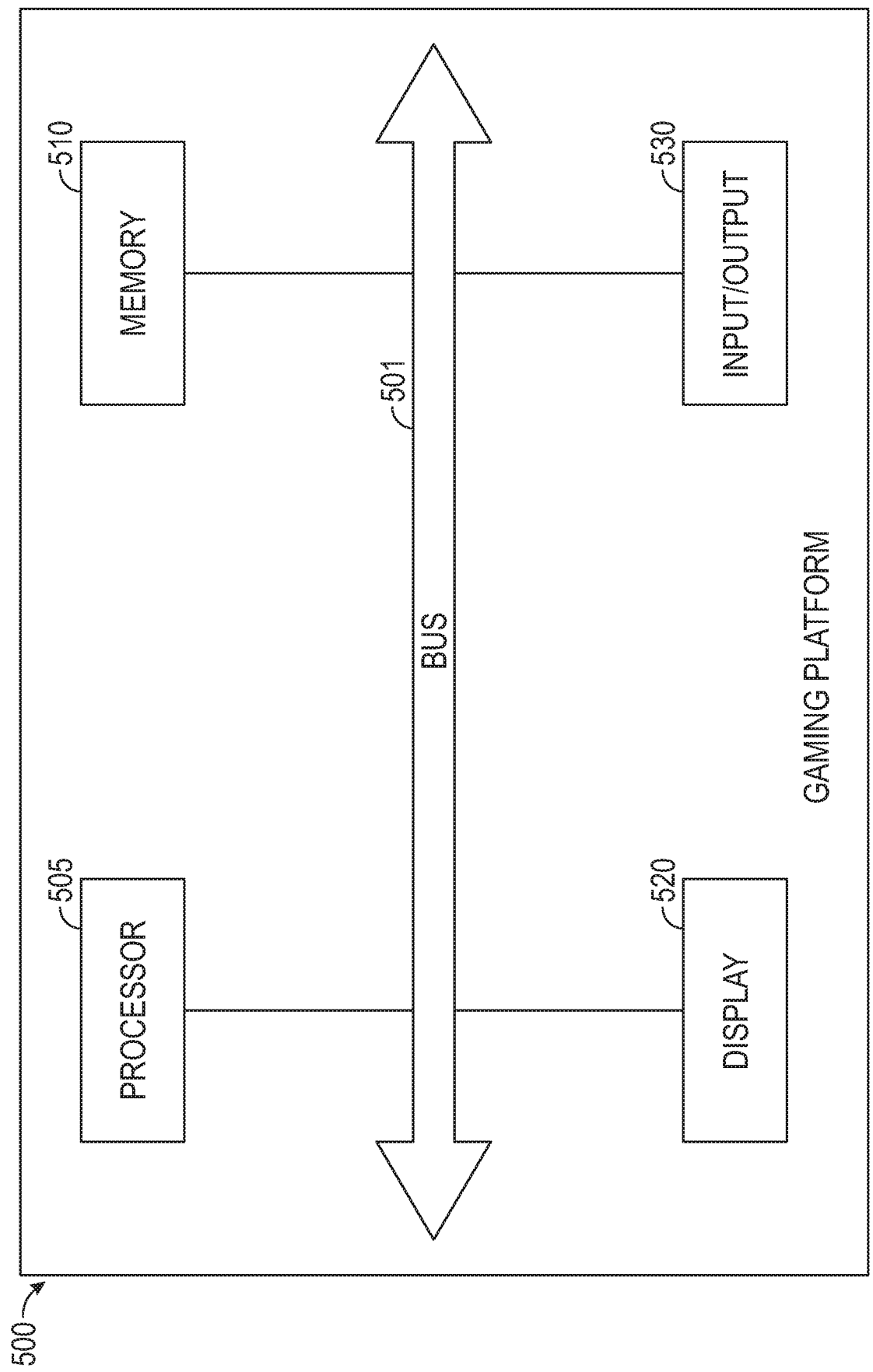
FIG. 5 shows a block diagram of a gaming platform.

FIG. 5 shows a block diagram of a gaming platform 500 including exemplary internal hardware for a game console, computer or other device that may be used to perform the methods described herein. For example, the hardware may be used to contain or implement the modules and/or process steps discussed above in reference to FIGS. 1-4.

A bus 501 may serve as the main data backbone interconnecting the other illustrated components of the hardware system 500. The processor 505 may be any processor or combination of processors or the like suitable for performing calculations, logical operations and so forth to execute a program such as the game program, biofeedback application or other programs contemplated herein, as well as any operating system or other software environment for such programs. The memory 510 may include a read only memory (ROM), random access memory (RAM), removable memory, bulk storage or any other volatile or non-volatile data storage for storing program code, program data and so forth. Program instructions, software or interactive modules may be stored in the memory 510.

A display 520 may be coupled to the processor 505 and other system components to provide a graphical output to a user including without limitation any data in audio, visual, graphic or alphanumeric format. Communication with external devices may occur using various communication ports, wireless communication interfaces, peripheral connections and so forth, collectively illustrated in FIG. 5 as input/output 530. This may, for example, include a serial port, an RS-232 port, a USB port, an RS-485 port, a VGA connector, and HDMI connector, or any other audio, visual, data or other input/output connectors. This may also or instead include wireless interfaces such as infrared, short-range radio frequency, or other interfaces suitable for coupling to peripherals, controllers, networks, other computers and so forth. The input/output 530 may more specifically include physical and/or logical interfaces for devices such as a keyboard, a mouse, a joystick, a touch screen, a remote control, a pointing device, a camera or other video input device, audio input and output, and so forth, any of which may be configured to receive user input and provide user output for providing a biofeedback, therapeutic gameplay system as contemplated herein.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method comprising:
    receiving an assessment of a person, the assessment including an evaluation of a trait of the person and an evaluation of an emotional or behavioral impairment of the person independent from the trait of the person;
    selecting a game, from one or more computer games, suitable for the person based on the assessment, the game having a variable difficulty, wherein selecting the game includes selecting a computer game from the one or more computer games suitable for the trait of the person such that the game construct is not inherently more challenging for the trait in a manner that interferes with managing a variable, biofeedback-based game difficulty, and wherein selecting the game includes selecting the game independently from a selection of user-specific therapeutic content including a pattern for varying a difficulty of the game according to a therapeutic strategy for the emotional or behavioral impairment;
    monitoring a physiological response of the person while playing the game with a sensor that acquires biofeedback from the person;
    varying a difficulty of the game with a processor using a pattern based on the emotional or behavioral impairment;
    measuring a change in the physiological response as the difficulty of the game changes; and
    modifying the difficulty of the game using effects controlled independently from gaming software for the game to increase the difficulty when the physiological response exceeds a predetermined threshold characteristic of the emotional or behavioral impairment, wherein modifying the difficulty of the game includes monitoring game output from an application programming interface for the gaming software and modifying the difficulty of the game in response to the game output.

2. The method of claim 1 wherein the trait includes at least one of a fine motor control, a gross motor control, and a cognitive performance skill.

3. The method of claim 1 wherein selecting a computer game includes selecting a plurality of computer games and presenting the plurality of computer games to the person as options for gameplay.

4. The method of claim 1 wherein the assessment includes at least one of a series of questions about the person, a structured evaluation of the person, and a clinical evaluation of the person.

5. The method of claim 1 wherein selecting the game includes selecting a computer game suitable for a motor skill of the person.

6. The method of claim 1 wherein the physiological response includes a heart rate or a breathing rate.

7. The method of claim 1 wherein the pattern for varying the difficulty of the game is selected to teach the person improved management of the emotional or behavioral impairment.

8. The method of claim 1 wherein modifying the difficulty includes displaying an overlay that obscures a portion of the game presented on a display of a computer.

9. The method of claim 8 further comprising concurrently displaying an indicator of a degree of manifestation of the emotional or behavioral impairment.

10. The method of claim 8 wherein the overlay includes a smoke effect.

11. The method of claim 10 wherein the smoke effect rises from a bottom of the display to cover an increasing portion of the display as the physiological response indicates increasing manifestation of the emotional or behavioral impairment.

12. The method of claim 1 wherein modifying the difficulty includes superimposing a graphical element over at least a portion of the game presented on a display of a computer.

13. The method of claim 1 wherein the effects include a video overlay of visual effects.

14. The method of claim 13 wherein modifying the difficulty of the game includes writing the video overlay of visual effects directly to a display or a video buffer.

15. The method of claim 13 wherein the effects are rendered within active regions of a game window independently from, but correlated with visual content of, a current game.

16. The method of claim 1 further comprising monitoring game output by programmatically monitoring visual display of an in-progress game and modifying the difficulty of the game in response to the game output.

17. The method of claim 1 wherein modifying the difficulty of the game includes altering an audio of the game during gameplay.

18. The method of claim 1 wherein modifying the difficulty of the game includes modifying a responsiveness of a user input device during game play.

19. A computer program product for remediating emotional or behavioral impairments, the computer program product comprising computer executable code embodied in a non-transitory computer-readable medium that, when executing on one or more computing devices, performs the steps of:
    receiving an assessment of a person, the assessment including an evaluation of a trait of the person and an evaluation of an emotional or behavioral impairment of the person;
    selecting a game, from one or more computer games, suitable for the person based on the assessment, the game having a variable difficulty, wherein selecting the game includes selecting a computer game from the one or more computer games suitable for the trait of the person such that the game construct is not inherently more challenging for the trait in a manner that interferes with managing a variable, biofeedback-based game difficulty, and wherein selecting the game includes selecting the game independently from a selection of user-specific therapeutic content including a pattern for varying a difficulty of the game according to a therapeutic strategy for the emotional or behavioral impairment;

monitoring a physiological response of the person while playing the game with a sensor that acquires biofeedback from the person;

varying a difficulty of the game using a pattern based on the emotional or behavioral impairment;

measuring a change in the physiological response as the difficulty of the game changes; and modifying the difficulty of the game using effects controlled independently from gaming software for the game to increase the difficulty when the physiological response exceeds a predetermined threshold characteristic of the emotional or behavioral impairment, wherein modifying the difficulty of the game includes monitoring game output from an application programming interface for the gaming software and modifying the difficulty of the game in response to the game output.

20. A system comprising:

a display;

a processor;

a physiological monitor configured to provide a physiological signal, the physiological monitor coupled in a communicating relationship with the processor; and a memory storing an assessment of a person, the assessment including an evaluation of a trait of the person and an evaluation of an emotional or behavioral impairment of the person, wherein the memory and processor are configured by computer executable code to perform the steps of selecting a game, from one or more computer games, suitable for the person based on the assessment, the game having a variable difficulty, wherein selecting the game includes selecting a computer game from the one or more computer games suitable for the trait of the person such that the game construct is not inherently more challenging for the trait in a manner that interferes with managing a variable, biofeedback-based game difficulty, and wherein selecting the game includes selecting the game independently from a selection of user-specific therapeutic content including a pattern for varying a difficulty of the game according to a therapeutic strategy for the emotional or behavioral impairment, presenting the game on the display, monitoring a physiological response of the person while playing the game based on the physiological signal from the physiological monitor, varying a difficulty of the game using a pattern based on the emotional or behavioral impairment, measuring a change in the physiological response as the difficulty of the game changes, and modifying the difficulty of the game using effects controlled independently from gaming software for the game to increase the difficulty when the physiological response exceeds a predetermined threshold characteristic of the emotional or behavioral impairment, wherein modifying the difficulty of the game includes monitoring game output by programmatically monitoring visual display of an in-progress game and modifying the difficulty of the game in response to the game output.

21. A method comprising:

receiving an assessment of a person, the assessment including an evaluation of a trait of the person and an evaluation of an emotional or behavioral impairment of the person independent from the trait of the person;

selecting a game, from one or more computer games, suitable for the person based on the assessment, the game having a variable difficulty, wherein selecting the game includes selecting a computer game from the one or more computer games suitable for the trait of the person such that the game construct is not inherently more challenging for the trait in a manner that interferes with managing a variable, biofeedback-based game difficulty, and wherein selecting the game includes selecting the game independently from a selection of user-specific therapeutic content including a pattern for varying a difficulty of the game according to a therapeutic strategy for the emotional or behavioral impairment;

monitoring a physiological response of the person while playing the game with a sensor that acquires biofeedback from the person;

varying a difficulty of the game with a processor using a pattern based on the emotional or behavioral impairment;

measuring a change in the physiological response as the difficulty of the game changes; and modifying the difficulty of the game using effects controlled independently from gaming software for the game to increase the difficulty when the physiological response exceeds a predetermined threshold characteristic of the emotional or behavioral impairment, wherein modifying the difficulty of the game includes monitoring game output by programmatically monitoring visual display of an in-progress game and modifying the difficulty of the game in response to the game output.

* * * * *

UNITED STATES PATENT AND TRADEMARK OFFICE
CERTIFICATE OF CORRECTION

PATENT NO. : 11,130,064 B2
APPLICATION NO. : 15/651814
DATED : September 28, 2021
INVENTOR(S) : Kahn, II et al.

Page 1 of 1

It is certified that error appears in the above-identified patent and that said Letters Patent is hereby corrected as shown below:

On the Title Page

Item (57), Abstract on Lines 8-9, delete "with requiring direct computation access to the executing game code" and insert -- without requiring direct computation access to the executing game code --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*